US009456854B1

(12) United States Patent
Powell

(10) Patent No.: US 9,456,854 B1
(45) Date of Patent: Oct. 4, 2016

(54) SPINOUS PROCESS CLAMP AND FIXATION DEVICE

(71) Applicant: N. Garrett Powell, Nashville, TN (US)

(72) Inventor: N. Garrett Powell, Nashville, TN (US)

( * ) Notice: Subject to any disclaimer, the term of this patent is extended or adjusted under 35 U.S.C. 154(b) by 0 days.

(21) Appl. No.: 13/652,290

(22) Filed: Oct. 15, 2012

Related U.S. Application Data

(63) Continuation-in-part of application No. 12/272,413, filed on Nov. 17, 2008, now Pat. No. 8,287,569.

(60) Provisional application No. 61/003,223, filed on Nov. 15, 2007.

(51) Int. Cl.
*A61B 17/70* (2006.01)

(52) U.S. Cl.
CPC ....... *A61B 17/7047* (2013.01); *A61B 17/7068* (2013.01)

(58) Field of Classification Search
CPC .................................................. A61B 17/7068
USPC ......................................... 606/248, 250–252
See application file for complete search history.

(56) References Cited

U.S. PATENT DOCUMENTS

| | | | |
|---|---|---|---|
| 4,573,454 A * | 3/1986 | Hoffman .................... 606/250 |
| 7,591,837 B2 | 9/2009 | Goldsmith | |
| 7,922,750 B2 * | 4/2011 | Trautwein et al. .......... 606/279 |
| 8,419,772 B2 * | 4/2013 | Thompson et al. ......... 606/254 |
| 8,562,650 B2 * | 10/2013 | Dace ............................. 606/248 |
| 8,591,548 B2 * | 11/2013 | Fiorella ........................ 606/249 |
| 2008/0021466 A1 * | 1/2008 | Shadduck et al. ............. 606/61 |
| 2008/0177326 A1 * | 7/2008 | Thompson .................... 606/277 |
| 2008/0243186 A1 * | 10/2008 | Abdou .......................... 606/246 |
| 2008/0281359 A1 * | 11/2008 | Abdou .......................... 606/246 |
| 2010/0241169 A1 * | 9/2010 | Liu et al. ...................... 606/263 |
| 2012/0283778 A1 * | 11/2012 | Yeh ............................... 606/250 |
| 2013/0096614 A1 * | 4/2013 | Zhang .......................... 606/250 |
| 2013/0103088 A1 * | 4/2013 | Karahalios et al. ......... 606/248 |
| 2014/0074166 A1 * | 3/2014 | Scarrow et al. ............. 606/247 |

* cited by examiner

*Primary Examiner* — Ellen C Hammond
(74) *Attorney, Agent, or Firm* — Waller Lansden Dortch & Davis, LLP; Matthew C. Cox

(57) ABSTRACT

A modular system for fixation of a spinous process includes at least one pair of blocks shaped so as to engage a particular segment of the spinous process and arranged on opposing sides of the spinous process. Each block has a surface facing the portion of the spinous process to be engaged, the surface having an array of sharp spikes to penetrate the spinous process when so engaged. Two rods arranged parallel to the spinous process are provided to connect the at least one pair of blocks and therefore stabilize multiple segments of the spinous process. Each block includes an aperture within a central portion of the block and shaped so as to slidably receive one of the rods. Set screws are provided so as to securely position the block along the length of the rod.

15 Claims, 13 Drawing Sheets

SPINOUS PROCESS CLAMP AND FIXATION DEVICE

CROSS-REFERENCES TO RELATED APPLICATIONS

This application claims benefit of the following patent applications which are hereby incorporated by reference: co-pending U.S. patent application Ser. No. 12/272,413 filed Nov. 17, 2008, and U.S. Provisional Application No. 61/003,223 filed Nov. 15, 2007.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND

The present invention relates generally to a system and method for fixation of a spinous process. More particularly, this invention pertains to stabilization of the human spine by applying a system and method to the applicable vertebrae and associated tissue of the spinal column.

Systems for spinal fixation and stabilization are well established in a wide variety of embodiments. Examples in which such systems are generally used to apply force to the spinal column include correcting degenerative conditions or deformities, maintaining a proper structural environment in the healing process from traumatic surgery, or providing temporary but secure positioning of the spine to facilitate the implanting of further components for performing the same functions. Where invasive surgery has been performed, the systems are generally intended to reliably maintain such fixation of the treated spinal process post-operatively so that bony fusion of the vertebrae of other equivalent functions may be achieved.

Early systems performing these functions comprised spinous process wiring. These systems were adequate in preventing flexion but led to relatively poor fixation, particularly in the cervical region of the vertebral column, because they still permitted rotation or extension of the affected region to some extent. This mechanical deficiency is particularly apparent in patients having osteoporosis, as one prominent example.

Other fixation systems have been anchored to a portion of the spinal process using lateral bone mass screws. These systems simply screw components directly into the bone to increase stability. Plates or rods may be utilized to fuse adjacent segments of the spine. However, there are additional problems associated with this method. The bone of the spinous process may be too soft to maintain immobility of the process over time and with increased activity. The method carries some attendant risk of major complications such as vertebral artery or root nerve injury. Further, lateral mass screw fixation systems are technically demanding and therefore may be quite inconvenient to implant and/or to remove.

More recently, systems have been developed to compress portions of the spinous process by sandwiching the processes between a plurality of plates. These plates are tightened with screws that extend through the plates and may or may not contact the spinous process itself, as desired or necessary under the circumstances. Generally speaking, these processes have improved stability without most of the limitations or inconveniences of the previous systems. However, these systems remain troublesome or inadequate where circumstances require fusion of spinous processes having a variety of dimensions, such as where the affected regions range across multiple bodies of vertebrae. Where subjects of variable sizes are involved such as large adults versus small children the problems may be pronounced further.

What is needed, therefore, is a modular system that may reliably perform the necessary function of stabilizing a portion of the spinous process, and that may flexibly adapt to spinous processes of varying sizes and needs.

There is a further need that the system be able to stabilize multiple adjacent levels of the spinal column, while allowing for safe, quick and convenient implantation and removal of the system.

BRIEF SUMMARY

In one aspect of the present invention, a modular system for fixation of a spinous process includes a plurality of blocks, each block ideally shaped so as to engage a particular segment of the spinous process. The blocks comprise at least one pair of blocks, with each pair arranged on opposing sides of the spinous process. Each block has a surface facing the portion of the spinous process to be engaged, the surface having an array of sharp spikes or otherwise acicular members. A clamping device may be further provided to perform the preliminary task of compressing the blocks against the spinous process. The spikes may penetrate the spinous process and further stabilize the blocks in place upon the spinous process when the blocks are compressed against the spinous process member.

In some embodiments, the present invention provides a spinous process clamp apparatus configured for attachment to first and second longitudinal rods positioned on opposite sides of a spinous process member. The apparatus includes a primary block including a primary rod channel defined entirely through the primary block. The primary rod channel is shaped for receiving the first longitudinal rod. A secondary block is positioned opposite the primary block. The secondary block includes a secondary rod channel defined entirely through the secondary block. The secondary rod channel is shaped for receiving the second longitudinal rod. The primary and secondary blocks are configured to apply compressive forces against opposite sides of the spinous process member when the spinous process member is positioned between the primary and secondary blocks.

In additional embodiments, the present invention provides a spinous process fixation device for attachment to at least one spinous process member. The device includes a first longitudinal rod and a second longitudinal rod oriented substantially parallel to the first longitudinal rod. A primary block is disposed on the first longitudinal rod, and a secondary block is disposed on the second longitudinal rod opposite the primary block. A gap is defined between the primary and secondary blocks configured to receive the spinous process member. A clamp post spans the gap between the primary and secondary blocks. The primary and secondary blocks are configured to apply compressive forces against opposite sides of the spinous process member.

In further embodiments, the present invention provides a spinous process fixation device for attachment to a plurality of spinous process members. The device includes a first longitudinal rod and a second longitudinal rod oriented substantially parallel to the first longitudinal rod. A plurality of spinous process clamps is disposed on the first and second longitudinal rods. Each spinous process clamp includes a primary block disposed on the first longitudinal rod and a secondary block disposed on the second longitudinal rod opposite the primary block. Each spinous process clamp includes a gap defined between the primary and secondary blocks configured for receiving one of the plurality of spinous process members; and each spinous process clamp includes a clamp post spanning the gap between the primary and secondary blocks.

Numerous other objects, features and advantages of the present invention will be readily apparent to those skilled in the art upon a reading of the following disclosure when taken in conjunction with the accompanying drawings.

DETAILED DESCRIPTION

Figure 1:
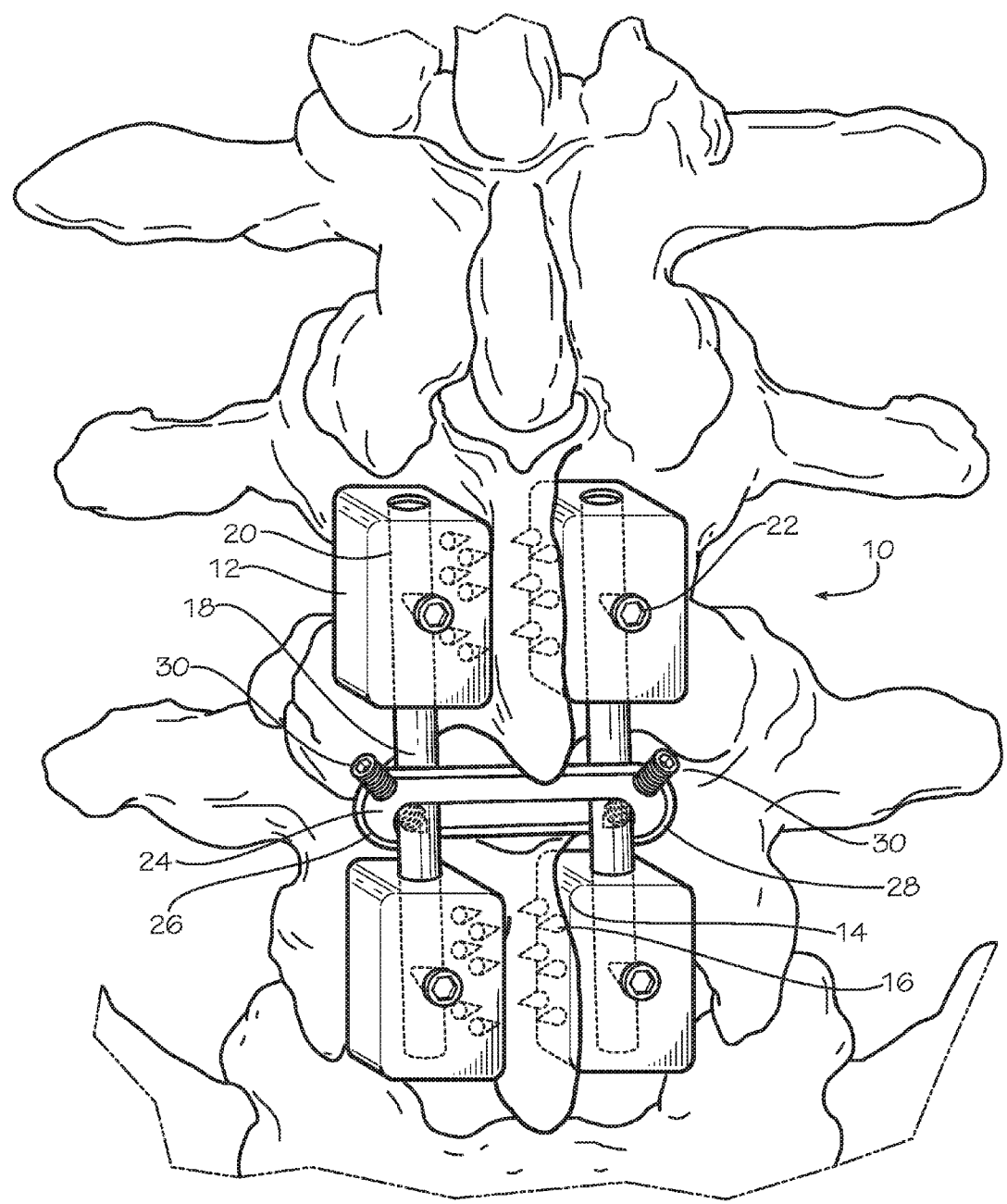
FIG. 1 is a posterior cross-sectional view of a first embodiment of the system of the present invention attached to a portion of a spinal column.
Figures 2, 3:
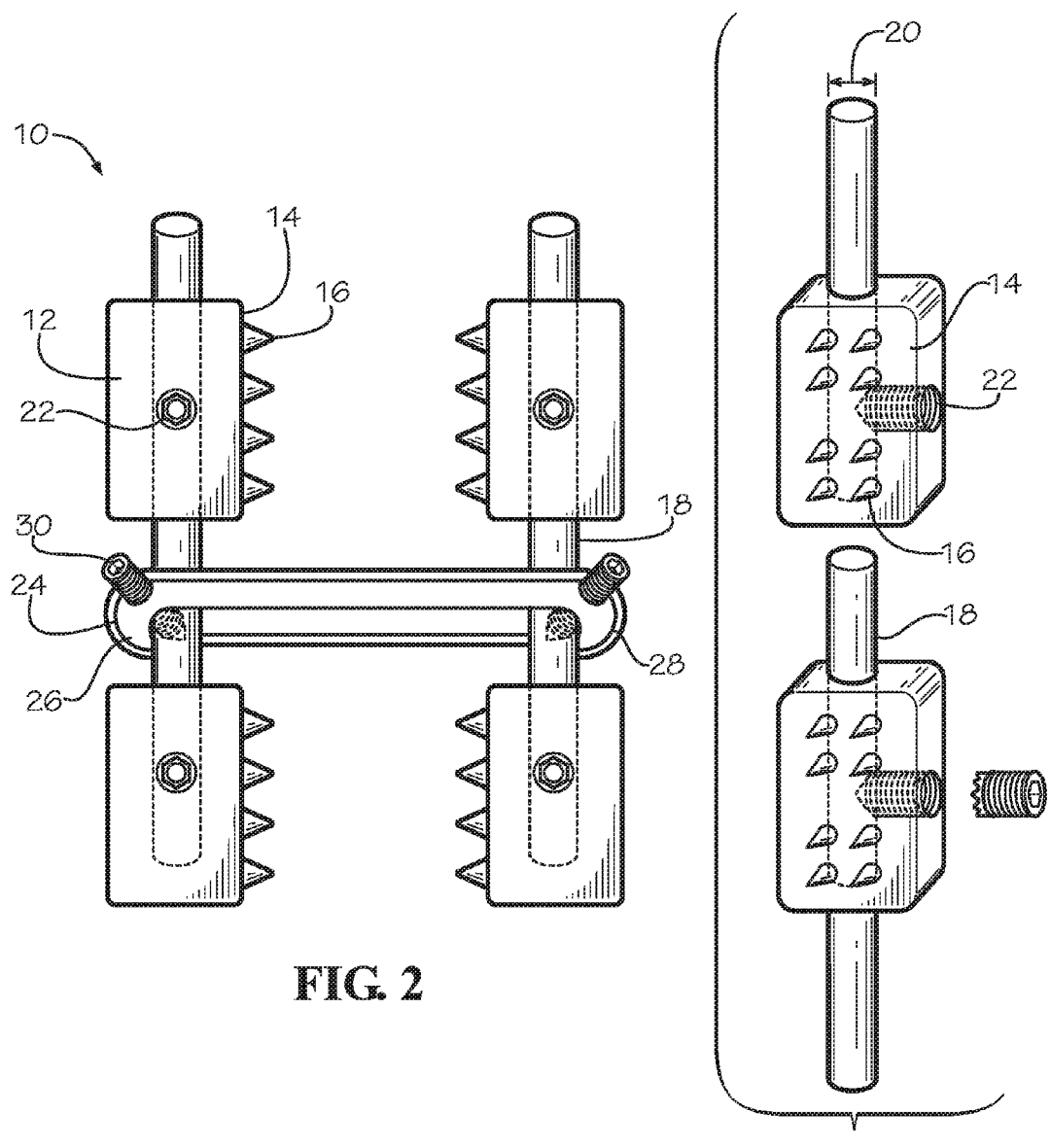
FIG. 2 is a posterior view of the system of FIG. 1 standing alone.
FIG. 3 is a partially exploded side cross-sectional view of blocks and rods of the system of FIG. 1 standing alone.

Referring generally now to FIGS. 1-5, the modular spinous process fixation system 10 of the present invention attaches to one or more particular spinous processes of a spinal column. The system 10 operates to rapidly and efficiently stabilize adjacent levels of the spinal column or vertebral column to allow for fusion or other indicated objectives. The modularity of the system 10 ensures that components are interchangeable to accommodate the variable shapes and sizes of spinous processes located among the separate portions of the vertebral column. Modularity is further desirable to accommodate varying sizes of individuals, such as pediatric patients for example, or spinous processes located within subjects of various states of spinal degeneration or deformity. It is contemplated as well that the system 10 may comprise components of variable length to span one or more interspaces and therefore accommodate the need to stabilize multiple adjacent segments of the vertebral column.

According to one embodiment of the system 10 of the present invention, a plurality of blocks 12 is provided, the blocks 12 being appropriately sized and shaped and having a facing surface 14 intended to operatively engage an associated segment of the spinous process. It is contemplated that the facing surface 14 itself may be designed, for example being grooved, serrated or otherwise roughly composed, such that it engages the spinous process when compressive force is applied and operates to prevent rotation or other undesired movement. However, in preferred embodiments of the present invention the facing surface 14 further comprises an array of acicular members 16. These acicular members 16 will generally comprise sharp spikes 16, but may comprise teeth, serrations or other equivalent protrusions as well. It is contemplated that these spikes 16 may be integral to the blocks 12 or separately attached. The spikes 16 located on the facing surface 14 of each block 12 engage the spinous process and function to better maintain the stability and rigidity of the attachment. The spikes 16 will generally penetrate the bone of the spinous process in question, but this is not a required function.

The blocks 12 comprise at least one pair of blocks 12, with each pair arranged on opposing sides, generally to the left and to the right of the spinous process. The blocks 12 may be scaled in size to accommodate a variety of users such as large adults or pediatric patients. The blocks 12 may be further scaled in size to allow fixation to different parts of the spine, including cervical, thoracic and lumbar segments, or combinations of the above where desired or necessary.

In certain embodiments of the present invention, a clamping device (not herein displayed) may be provided for temporarily compressing each pair of blocks 12 against the spinous process and attaching the system 10 to the affected segments. In this way, the system 10 may be assembled during surgical implantation so as to quickly and effectively respond to needs as they arise. It is contemplated that the clamping device may be post-operatively removed once further compressive components or methods have been applied.

In preferred embodiments of the present invention, a pair of elongated members 18, such as rods 18, is provided having equivalent lengths. Each rod 18 is positioned parallel to the affected spinous processes and along a longitudinal axis generally corresponding to that of the spinal column. The lengths of the rods 18 are user-selectable so as to accommodate the entirety of the adjacent spinous processes to be stabilized. The rods 18 may further be adjusted by the surgeon user so as to acquire the desired length, as where needed to span multiple interspaces or to alternatively reduce length where redundant or otherwise unnecessary. This adjustment may be made by physically cutting the rods 18 or other equivalent functions as needed or as available under the associated conditions.

Each block 12 is shaped so as to facilitate attachment to one of the rods 18. In a preferred embodiment of the present invention, each block 12 has an aperture 20 extending at least partially through a central portion of the block 12 along a longitudinal axis, the aperture shaped so as to slidably receive one of the rods 18. Where the aperture 20 extends partially through the block 12, the block 12 may be oriented upon one end of the rod 18 or the opposing end. Where the aperture 20 extends fully through the block 12, the block 12 may be oriented at any position along the length of the rod 18 as desired or necessary under the circumstances.

Figure 4:
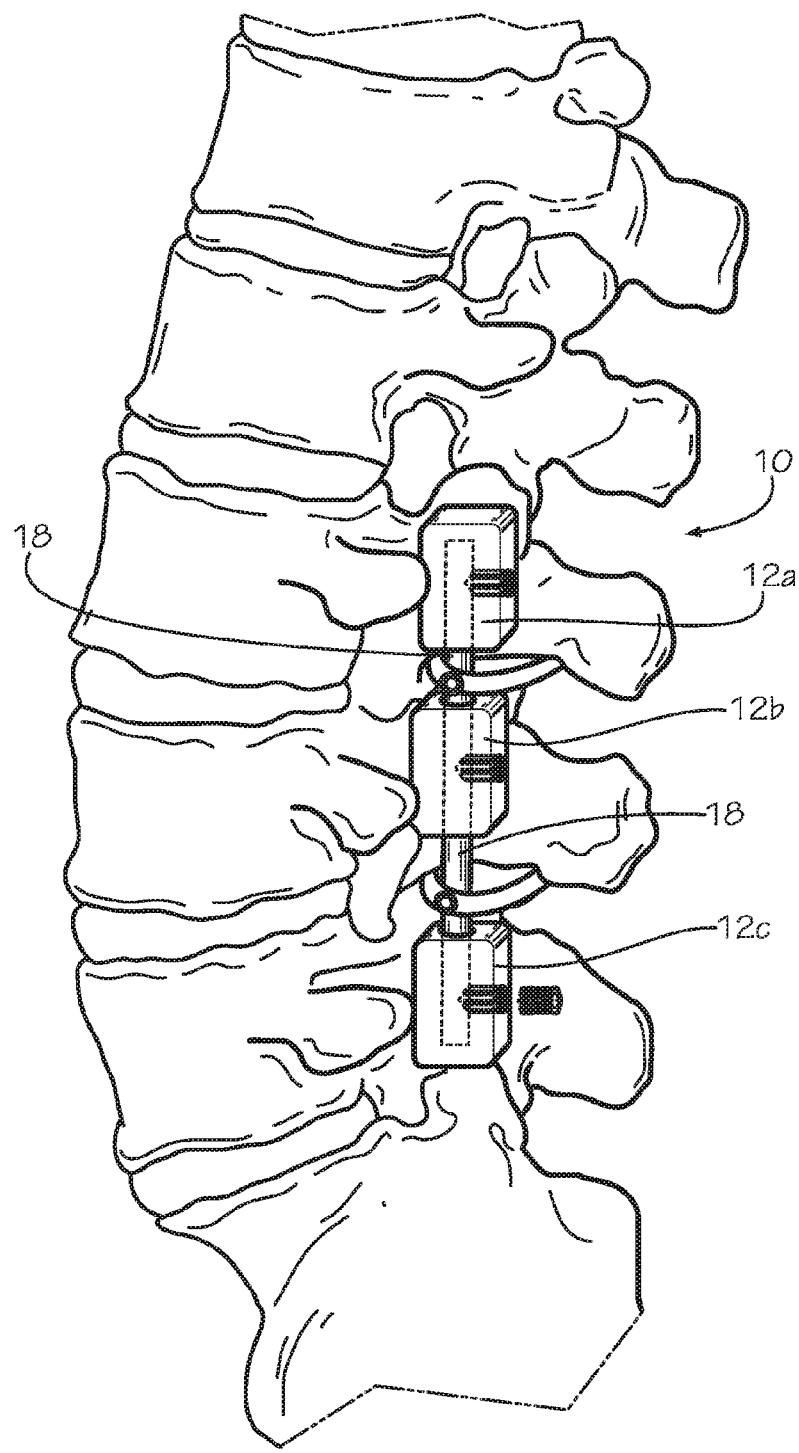
FIG. 4 is a side cross-sectional view of a second embodiment of the system of the present invention attached to a portion of a spinal column, demonstrating more than two blocks oriented along opposing sides of the spinal column.
Figure 5:
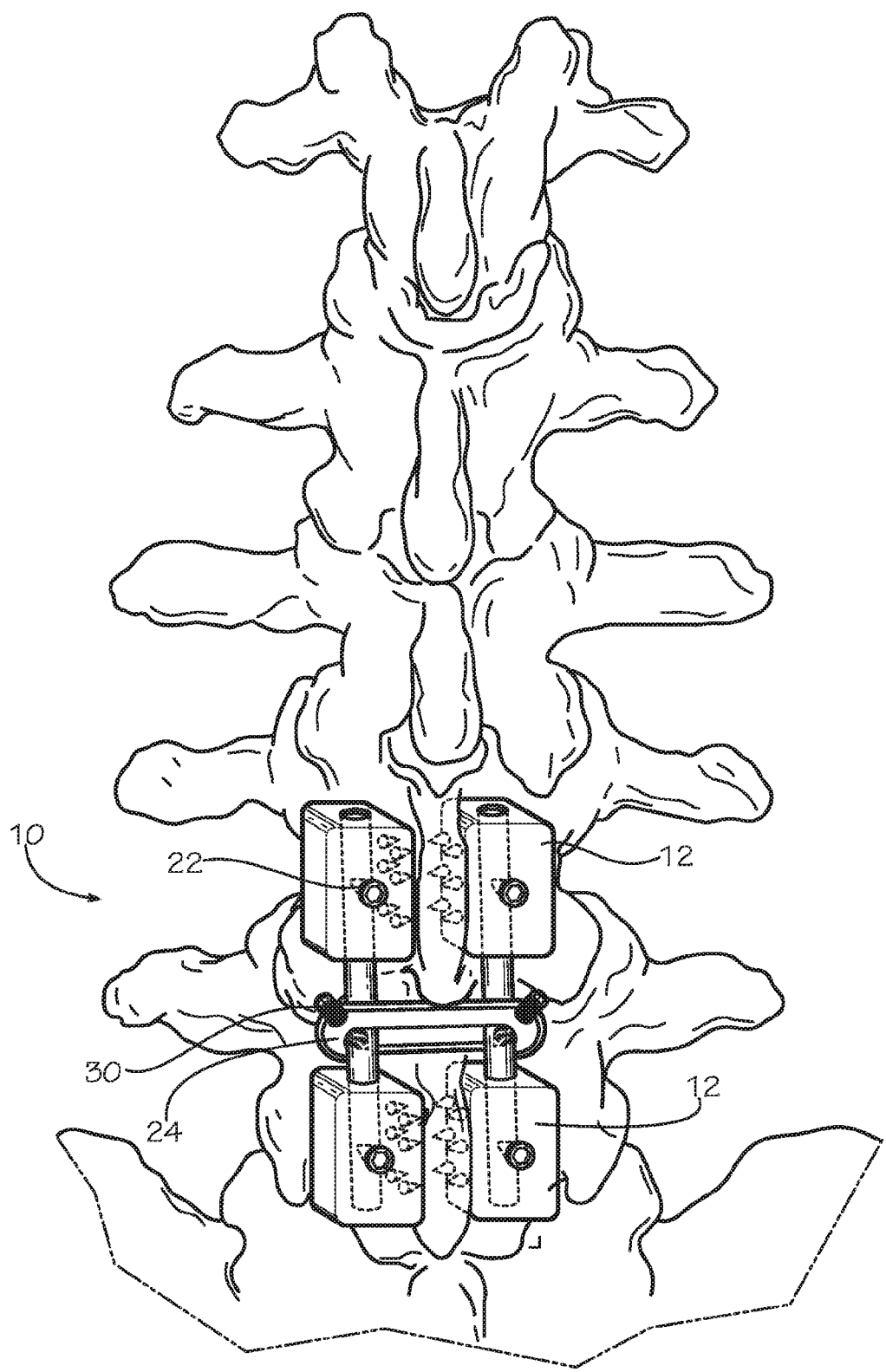
FIG. 5 is a posterior cross-sectional view of the system of FIG. 1 attached to a portion of a spinal column.

Referring to FIG. 4, an embodiment of the present invention is demonstrated wherein first and second blocks 12a, 12c are mounted upon opposing ends of each rod 18, and a third block 12b is further oriented at a third position along the length of each rod 18 between first and second blocks 12a, 12c. This embodiment specifically demonstrates the flexibility of the system 10, as many different levels of the spinal column may be spanned while allowing optimal placement of the blocks 12 on a given spinous process. The system 10 purports to negate the necessity of attaching multiple clamps or blocks 12 onto a single level of the vertebral column.

In the preferred embodiment, each block 12 further comprises a set screw 22 or similar fastening device 22 penetrating the block 12 along a latitudinal axis or otherwise transverse to the axis upon which the aperture 20 is located through which the rod 18 may pass. The set screw 22 operates to tighten the block 12 against the rod 18 when the block 12 has been oriented at a position along the length of the rod 18 as desired by the user or necessary under the circumstances. Various embodiments of tools with which to manipulate the set screws 22 may be contemplated to accommodate the varying conditions under which the system 10 is utilized.

In these embodiments of the present invention, the rods 18 are therefore aligned along the spinous process such that at least one pair of blocks 12 is securely attached to the rods 18. As displayed in FIG. 1, two pairs of blocks 12 are oriented upon opposing ends of the rods 18 and directly upon opposing sides of the spinous process requiring compression. Such compressive force at this juncture may equivalently be applied either against the blocks 12 or the rods 18.

In the preferred embodiment of the present invention, and still referring to FIG. 1, a cross link 24 is further provided that connects to one of the rods 18 on a first end 26 and connects to the other of the rods 18 on a second end 28. A pair of cross link set screws 30 or similar fastening components 30 are angularly oriented upon the first end 26 and the second end 28 of the cross link 24. The set screws 30 may be adjusted in either direction to apply compressive or distractive force against the rods 18 to which the cross link 24 is engaged. In this manner the system 10 may generally be tightened, upon application of each modular component in turn, to a desired level of torque by a user such as a surgeon. Various embodiments of tools with which to manipulate the set screws 30 may be contemplated to accommodate the varying conditions under which the system 10 is utilized.

In other embodiments of the system 10 of the present invention, multiple cross links 24 may be utilized to accommodate variable lengths of rods 18 where many levels of the vertebral column are to be spanned. A separate cross link 24 may be applied at each intervening interspace of the vertebral column. Each cross link 24 may be fixed in length, or adjustable to accommodate variable distances between parallel rods 18.

In embodiments of the present invention comprising the clamping device to preliminarily apply compressive force upon the blocks 12, said clamping device may subsequently be removed upon successful application of the cross link 24.

In particular embodiments of the present invention, the modular components of the system 10, including any of the plurality of blocks 12, the rods 18, the cross link 24, and the set screws 22, 30 are composed of titanium alloy. It is contemplated however that the modular components of the system 10 may alternatively be composed of a metal, polymer, fiber or other alloy or material as desired and as are known within the art.

In an alternative embodiment of the present invention, a method of stabilizing spinous processes within a spinal column is disclosed. At least one pair of spaced blocks 12 is provided to be positioned upon either side of the spinal column, where one or more spinous processes require stabilization. Each block 12 has a surface 14 that is oriented inwardly and generally conforms to the associated segment of the spinous process to be engaged. A plurality of acicular members 16, or spikes 16, is disposed upon the facing surface 14. A first rod 18 is then attached to each block 12 to be positioned along one side of the spinal processes. A second rod 18 is further attached to each block 12 to be positioned along the opposing side of the spinal processes. A cross link 24 or generally a link member 24 is then attached on a first end 26 to the first rod 18 and on a second end 28 to the second rod 18. The user then tightens the link member 24 against the rods 18 to a desired torque so as to securely engage the spinous processes between the blocks 12.

It may be contemplated that many of the steps of the method of this described embodiment of the present invention are preformed prior to implantation within the subject. It may be further contemplated that the user seeks to minimize the bulk of the assembly 10 and simplify positioning of the assembly 10 by tightening the cross link 24 as far as possible during implantation of the assembly 10. Distractive force may then be applied to spread the blocks 12 apart immediately prior to physically mounting the assembly 10 upon the spinous processes. The blocks 12 may then be compressed once again so as to drive the spikes 16 into the spinous process and arrive at the desired torque level.

In certain embodiments of the method of the present invention, each pair of blocks 12 may be positioned upon either side of the spinous processes of the subject and clamped in position against each spinous process prior to attaching the rods 18, so as to more effectively maintain the desired position of the blocks 12. In these embodiments, the modular components are generally assembled within the subject. Upon completion of the step of tightening the link member 24 against the rods 18 to a desired torque, the user may release the initial clamping device and remove said clamping device from the subject.

Figure 6:
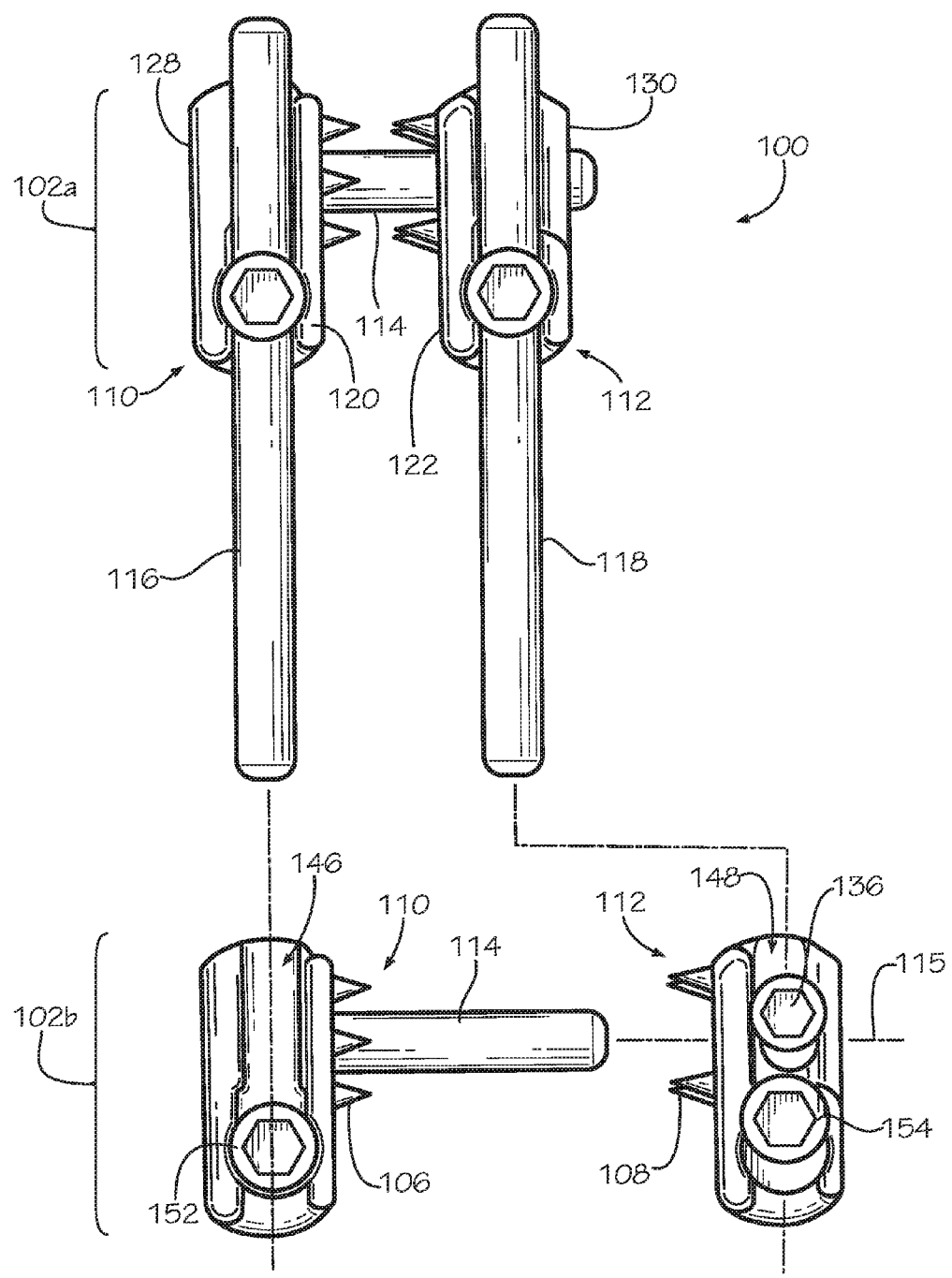
FIG. 6 is a partially exploded top plan view of an alternative embodiment of a spinous process fixation device in accordance with the present invention.

Referring now to FIG. 6, an additional embodiment of a spinous process fixation device 100 is illustrated. This embodiment includes at least one pair of opposing spaced blocks, or spinous process clamp 102, including a primary block 110 and a secondary block 112. Spinous process fixation device 100 in some embodiments includes two or more spinous process clamps 102a, 102b disposed on a pair of opposing longitudinal rods, including a first rod 116 and a second rod 118. The first and second rods 116, 118 are generally configured for positioning on opposite sides of multiple spinous process members 140a, 140b, as seen in FIG. 8.

Figure 8:
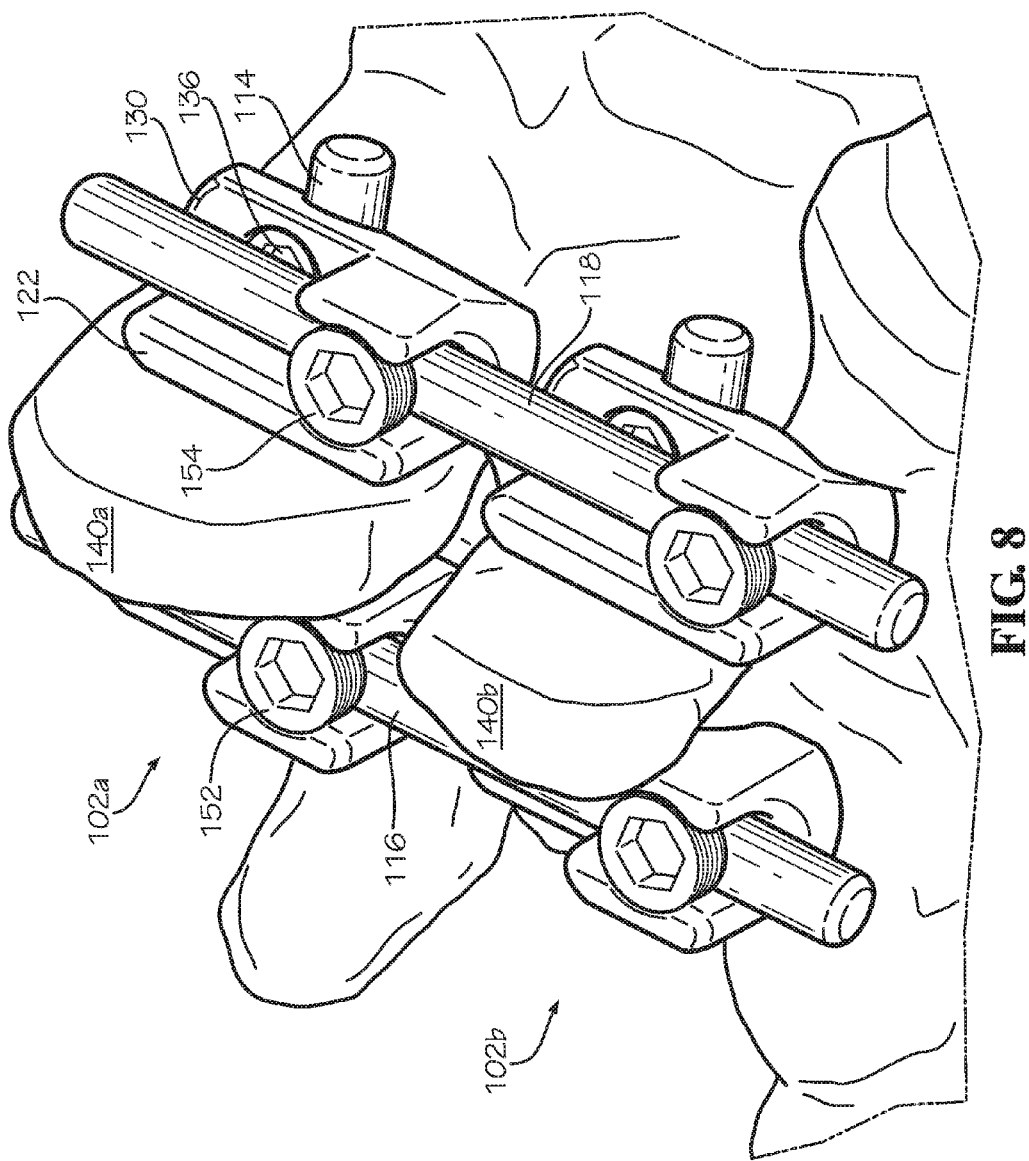
FIG. 8 is a perspective view of the embodiment of a spinous process fixation device of FIG. 6 installed on adjacent spinous process members.

In some embodiments, two or more spinous process clamps 102a, 102b, etc. are positioned on first and second rods 116, 118 for clamping adjacent spinous process members 140a, 140b as seen in FIG. 8. When clamped onto adjacent spinous process members as seen in FIG. 8, the spinous process fixation device 100 is generally operable to reduce the range of motion of a portion of the spine located near the fixation device.

Each spinous process clamp 102a includes a primary block 110 located opposite a secondary block 112. Primary block 110 includes a primary facing surface configured for positioning adjacent a first side of a first spinous process member. Primary facing surface 120 is shaped to directly engage a side of the first spinous process member and may include a substantially flat or shaped surface. Similarly, secondary block 112 includes a secondary facing surface 120 positioned to face toward the primary facing surface. Primary and secondary facing surfaces are positioned generally opposite one another for applying a clamping force against a spinous process member located therebetween. The primary and secondary facing surfaces include a substantially similar shape and include substantially equal surface areas for providing equal and opposing clamping forces in some embodiments.

Figure 7:
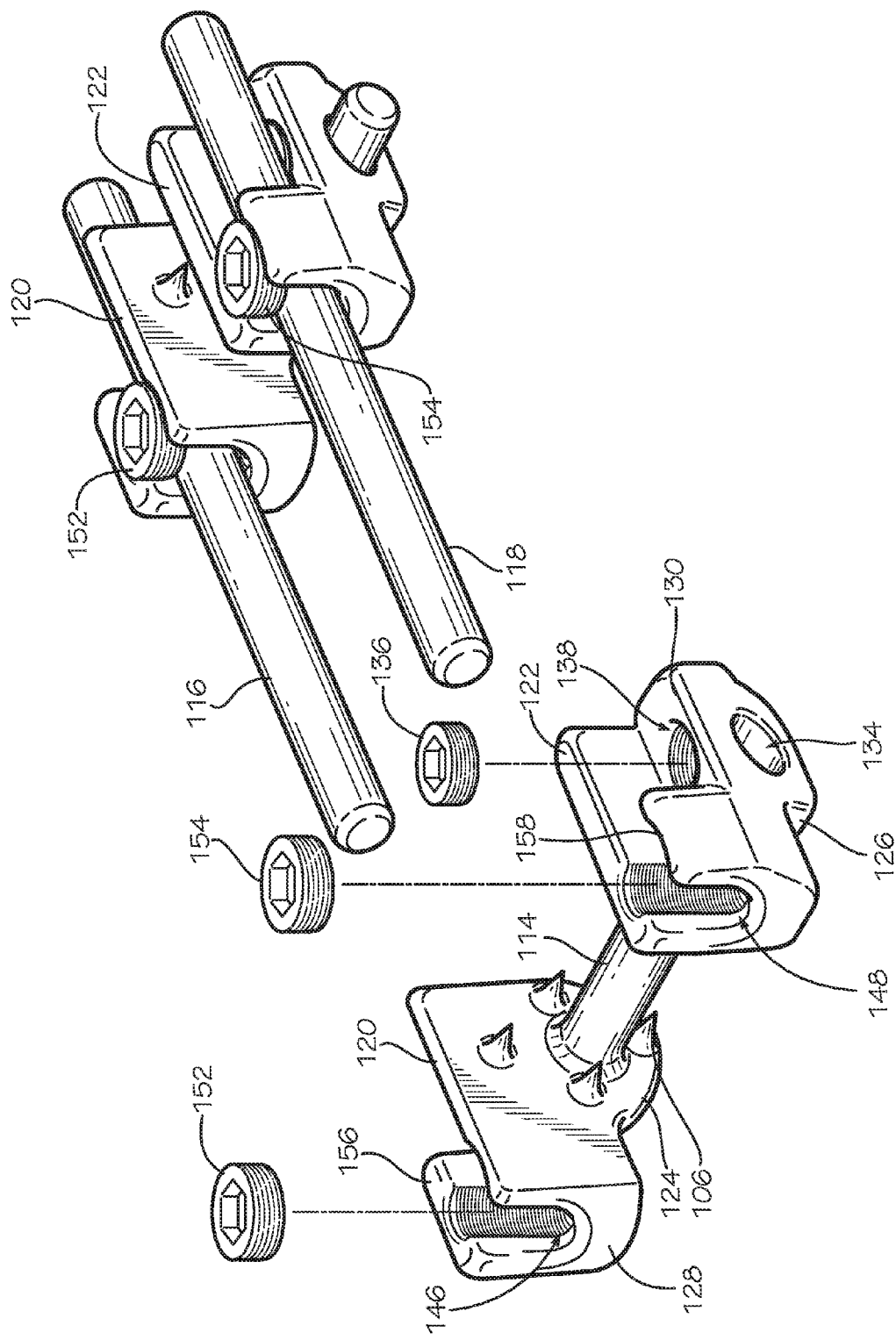
FIG. 7 is a partially exploded perspective view of the embodiment of a spinous process fixation device of FIG. 6.

Referring to FIG. 7, an embodiment of a spinous process clamp 120a includes a primary block 110 having several features. A primary clamp plate 120 has a generally rectangular shape in some embodiments and is oriented to be positioned substantially parallel to a spinous process member as seen in FIG. 8. Similarly, a secondary clamp plate 122 is disposed on secondary block 112. Secondary clamp plate 122 also includes a rectangular shape in some embodiments and is oriented to be positioned substantially parallel to a spinous process member on the side opposite primary clamp plate 120.

A primary extension 124 projects away from primary clamp plate 120 in a plane substantially parallel to primary clamp plate 120 in some embodiments. Primary extension 124 includes a substantially semicircular shape in some embodiments, as seen in FIG. 7. A secondary extension 126 also projects away from secondary clamp plate 122 generally opposite primary extension 124 in some embodiments. Secondary extension 126 also includes a substantially semicircular shape in some embodiments.

A plurality of primary spikes 106 project from primary clamp plate 120 generally toward secondary block 112; and a plurality of secondary spikes 108 project from secondary clamp plate 122 generally toward primary block 110. The spikes are configured to partially penetrate a spinous process member disposed between primary and secondary blocks 110, 112. As seen in FIG. 7, some of the primary spikes 106 are disposed on primary extension 124 surrounding and/or below clamp post 114. Primary spikes 106 generally do not extend from primary clamp plate 120 and/or primary extension 124 as far as clamp post 114.

As seen in FIGS. 6, 7, and 8, a clamp post 114 protrudes from primary block 110 toward secondary block 112 in some embodiments. Clamp post 114 is integrally formed on primary block 110 as a unitary, one-piece construction in some embodiments. Alternatively, clamp post 114 can be a separate component attached to primary block 110 using a fastener or any other suitable mechanical attachment. A corresponding clamp post socket 134 is defined on secondary block 112. Clamp post socket 134 includes a hole defined entirely through secondary block 112 in some embodiments. Clamp post 114 may be slidably received in clamp post socket 134 for securing primary and secondary blocks 110, 112 together. Clamp post 114 generally extends along a clamp post axis 115 oriented substantially perpendicular to first and second rods 116, 118 in some embodiments.

When clamp post 114 is received in clamp post socket 134, a clamp post fastener 136 may be installed in secondary block 112 to secure clamp post 114 at a fixed location in clamp post socket 134. Each clamp post fastener 136 includes a socket head set screw in some embodiments. A threaded clamp post fastener bore 138 is defined through secondary block 112 and is configured to threadedly receive a set screw in some embodiments. When primary and secondary blocks 110, 112 are located at a desired position pressing against opposite sides of a spinous process member, clamp post fastener 136 is tightened against clamp post 114 to selectively fix primary and secondary blocks 110, 112 relative to each other.

As seen in FIG. 6 and FIG. 7, a primary flange 128 extends transversely from primary clamp plate 120, forming an L-shaped body on primary block 110. Primary flange 128 is integrally formed as a unitary, one-piece construction on primary block 110 in some embodiments. Primary flange 128 projects from primary block 110 generally in a direction away from secondary block 112. During use, first rod 116 is positioned on the side of first clamp plate 120 opposite secondary block 112 such that first clamp plate 120 is located between first rod 116 and secondary block 112. Additionally, first rod 116 may engage the upper surface of primary flange 128. As such, first rod 116 is generally received against primary block 110 near the intersection of primary clamp plate 120 and primary flange 128. In some embodiments, primary flange 128 defines a U-shaped primary rod channel 146 in its upper surface, and first rod 116 is configured to be partially slidably received in primary rod channel 146. In some embodiments, the radius of curvature of first rod 116 is equal to or slightly smaller than the radius of curvature of primary rod channel 146. Primary rod channel 146 extends entirely through primary block 110 because primary rod channel 146 is open at both longitudinal ends as seen in FIG. 6 and FIG. 7.

A secondary flange 130 extends transversely from secondary clamp plate 122, forming an L-shaped body on secondary block 112. Secondary flange 130 is integrally formed as a unitary, one-piece construction on secondary block 112 in some embodiments. Secondary flange 130 projects from secondary block 112 generally in a direction away from primary block 110. During use, secondary rod 118 is positioned on the side of second clamp plate 122 opposite primary block 110 such that second clamp plate 122 is located between second rod 118 and primary block 110. Additionally, second rod 118 may engage the upper surface of secondary flange 130. As such, second rod 118 is generally received against secondary block 112 near the intersection of secondary clamp plate 122 and secondary flange 130. In some embodiments, secondary flange 130 defines a U-shaped secondary rod channel 148 on its upper surface, and second rod 118 is configured to be partially slidably received in secondary rod channel 148. In some embodiments, the radius of curvature of second rod 118 is equal to or slightly smaller than the radius of curvature of secondary rod channel 148. Secondary rod channel 148 extends entirely through secondary block 112 because primary rod channel 148 is open at both longitudinal ends as seen in FIG. 6 and FIG. 7.

As seen in FIG. 7 and FIG. 8, clamp post fastener 136 is generally dimensioned such that it does not extend above secondary flange 130 when disposed in clamp post fastener bore 138. As such, clamp post fastener 136 does not interfere with second rod 118 when second rod 118 is positioned against secondary flange 130 along secondary rod channel 148, and second rod 118 may be repositioned along secondary rod channel 148.

Referring further to FIGS. 6, 7 and 8, in some embodiments, a second rod fastener 154 is disposed on secondary block 112 to secure secondary block 112 at a desired location along second rod 118. Second rod fastener 154 includes a set screw or any other suitable fastener. As seen in FIG. 7, a secondary tab 158 protrudes upwardly from secondary flange 130 in spaced relation to secondary clamp plate 122. Secondary tab 158, and the portion of secondary clamp plate 122 facing secondary tab 158, both include threaded regions configured to allow second rod fastener 154 to be threadedly received therebetween and to be screwed downwardly toward and tightened against secondary rod 118, as seen in FIG. 8. When spinous process clamping device 100 is positioned on a patient, second rod fastener 154 can be slightly loosened to allow longitudinal and/or angular repositioning of secondary block 112 relative to second rod 118.

Similarly, a first rod fastener 152 is used in some embodiments to secure primary block 110 to first rod 116. First rod fastener 152 may include a set screw or any other suitable fastener. As seen in FIG. 7, a primary tab 156 protrudes upwardly from primary flange 128 in spaced relation to primary clamp plate 120. Primary tab 156 and the portion of primary clamp plate 120 facing primary tab 156 may include opposing threaded regions configured to allow first rod fastener 152 to be installed between primary tab 156 and primary clamp plate 120 and to be screwed downwardly toward and tightened against first rod 116.

Primary rod channel 146 includes a U-shaped channel that extends along the upper surface of primary flange 128 and also extends through the space between primary tab 156 and primary clamp plate 120. Similarly, secondary rod channel 148 includes a U-shaped channel that extends along the upper surface of secondary flange 130 and also through the space between secondary tab 158 and secondary clamp plate 122.

As seen in FIG. 8, first and second spinous process clamps 102a, 102b can be secured to first and second adjacent spinous process members 140a, 140b, respectively, to provide stabilization or fixation of associated tissue on the spinal column. Generally, during use, each clam post 114 is positioned to span between primary and secondary blocks 110, 112 at a location between the adjacent spinous process members 140a, 140b, as seen in FIG. 8. In some alternative embodiments, clamp post 114 can pierce the spinous process member and extend through the spinous process member as opposed to extending through the space between adjacent spinous process members. Once each clamp post fastener 136 is tightened against clamp post 114 in clamp post fastener socket 138, first and second rods 116, 118 may be positioned in primary and secondary rod channels 146, 148, respectively; and each first rod fastener 152 and second rod fastener 154 can be secured on each primary and secondary block 110, 112, respectively. In some embodiments, a portion of clamp post 114 may extend laterally beyond secondary block 112 when inserted through clamp post socket 134, as seen in FIG. 8. As such, clamp post socket 134 extends entirely laterally through secondary block 112 in some embodiments.

Referring to FIGS. 9-12, an alternative embodiment of a spinous process fixation apparatus 200 is generally illustrated in a partially exploded perspective view. Spinous process fixation apparatus 200 includes a plurality of spinous process clamps 202a, 202b, etc. Each spinous process clamp 202 can be alternatively described as a pair of opposing blocks. Each spinous process clamp 202a, 202b, etc. on a spinous process fixation device 200 may be identical to other spinous process clamps on the same device and/or interchangeable with other spinous process clamps in some embodiments.

Figure 11:
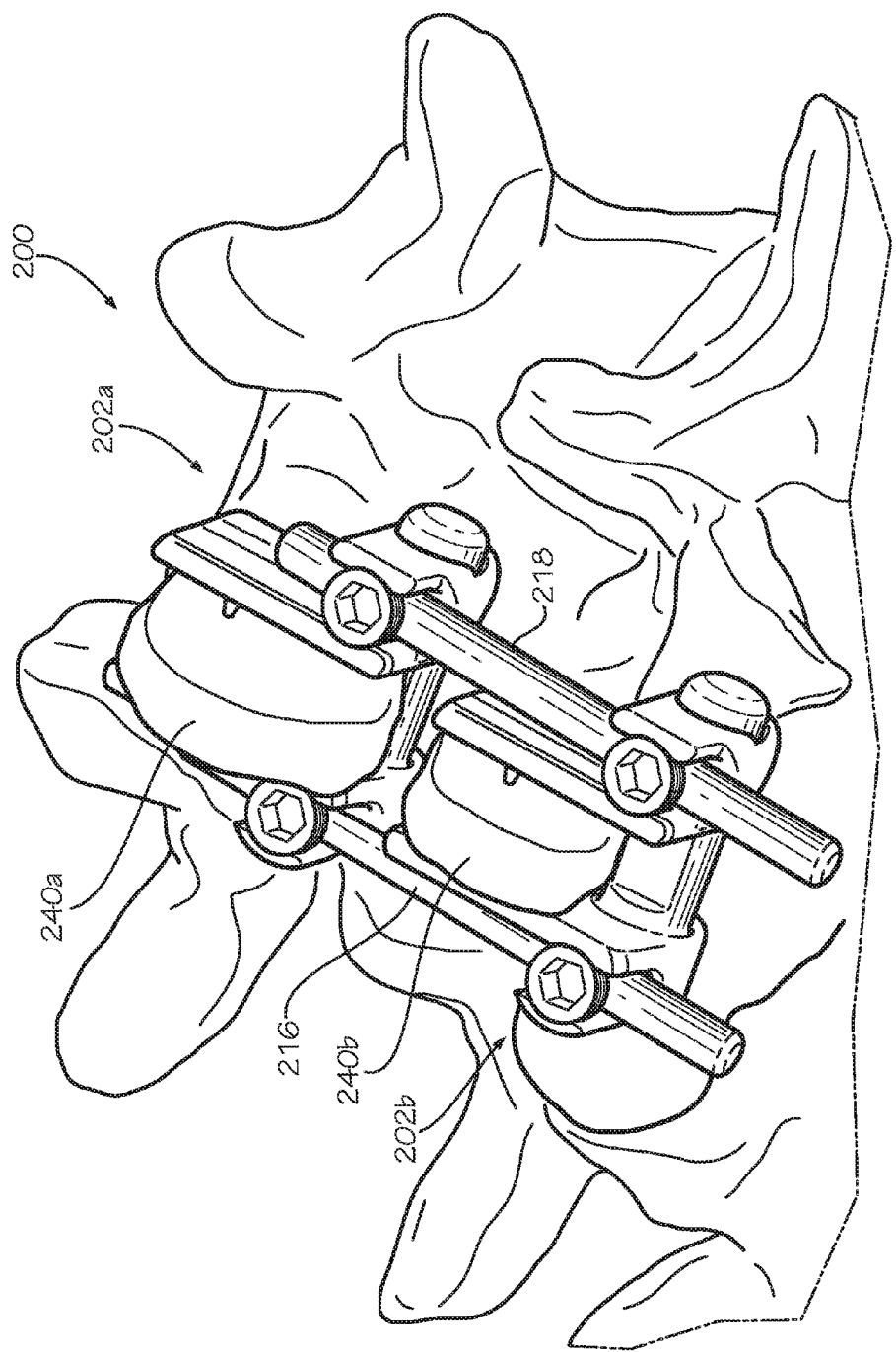
FIG. 11 is a perspective view of the embodiment of a spinous process fixation device of FIG. 9 installed on adjacent spinous process members.

Each spinous process clamp 202a, 202b includes a primary block 210 and a secondary block 212. Opposing primary block 210 and secondary block 212 are spaced from each other to provide a gap for positioning a spinous process member 240a, as seen in FIG. 11. A clamp post 214 spans the gap between primary block 210 and secondary block 212. Clamp post 214 extends from primary block 210 toward secondary block 212 in some embodiments. Clamp post 214 is received in a clamp post socket 234 defined on secondary block 212 in some embodiments.

A clamp post fastener 236 is disposed on secondary block 212 and may be tightened against clamp post 214 when clamp post 214 is positioned in clamp post socket 234. Clamp post fastener 236 is installed through a clamp post fastener bore defined in secondary block 212. In some embodiments, clamp post fastener 236 includes a set screw or any other suitable fastener. The clamp post fastener bore is generally open to clamp post socket 234 in some embodiments, as seen in FIG. 9, such that a portion of clamp post fastener 236 can extend into clamp post socket 234 and engage clamp post 214.

Figure 12:
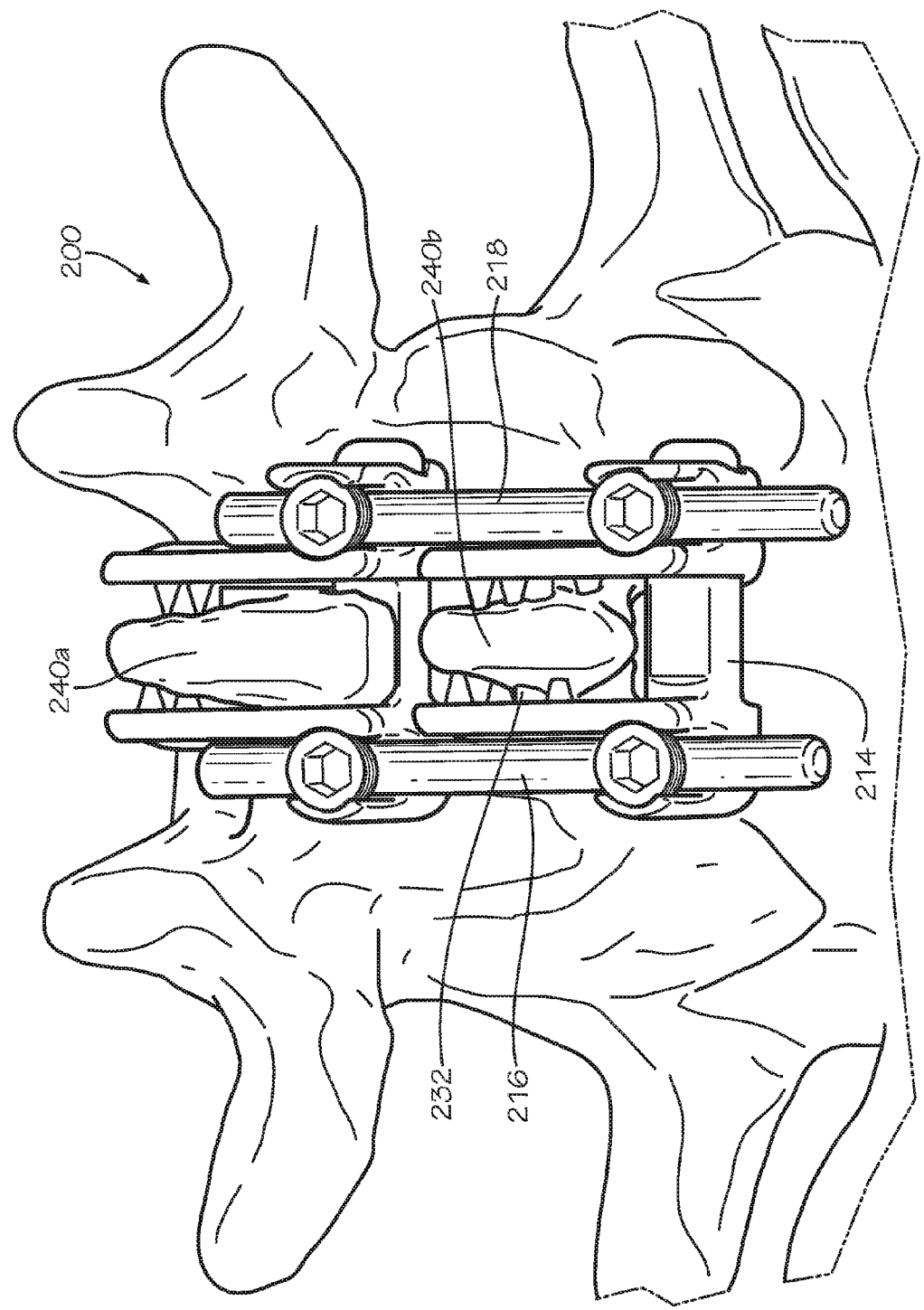
FIG. 12 is a top view of the embodiment of a spinous process fixation device of FIG. 9 installed on adjacent spinous process members.

Primary block 210 includes a substantially flat primary clamp plate 220 in some embodiments. Similarly, secondary block 212 includes an opposing substantially flat secondary clamp plate 222. Each primary and secondary clamp plate 220, 222 include facing clamping surfaces configured for clamping a spinous process member therebetween, as seen in FIG. 11 and FIG. 12. A plurality of primary spikes 206 extend from primary clamp plate 220 toward secondary clamp plate 222. Additionally, a plurality of secondary spikes 208 also extend from secondary clamp plate 222 generally toward primary clamp plate 220 in some embodiments. Each spike is configured to penetrate a small distance into a spinous process member located between the primary and secondary clamp plates 220, 222.

Additionally, in some embodiments, a fixation pin 232 protrudes from secondary clamp plate 222 on secondary block 212 toward primary clamp plate 220 on primary block 210. Fixation pin 232 includes a pointed or sharpened distal end configured for piercing through a spinous process member located between primary and secondary clamp plates 220, 222, as seen in FIG. 12. Fixation pin 232 may be partially received in a corresponding fixation pin socket 233 on primary clamp plate 220 in some embodiments. During use, secondary block 212 may be located beside a spinous process member and pressed toward the spinous process member such that the fixation pin 232 pierces the spinous process member and extends through the spinous process member until it extends through the other side and engages the fixation pin socket 233 on the primary block located on the opposite side of the spinous process member. As such, fixation pin 232 may be dimensioned to correspond to a predetermined spacing, or clamping distance, between primary and secondary blocks 210, 212 in some embodiments.

Figure 9:
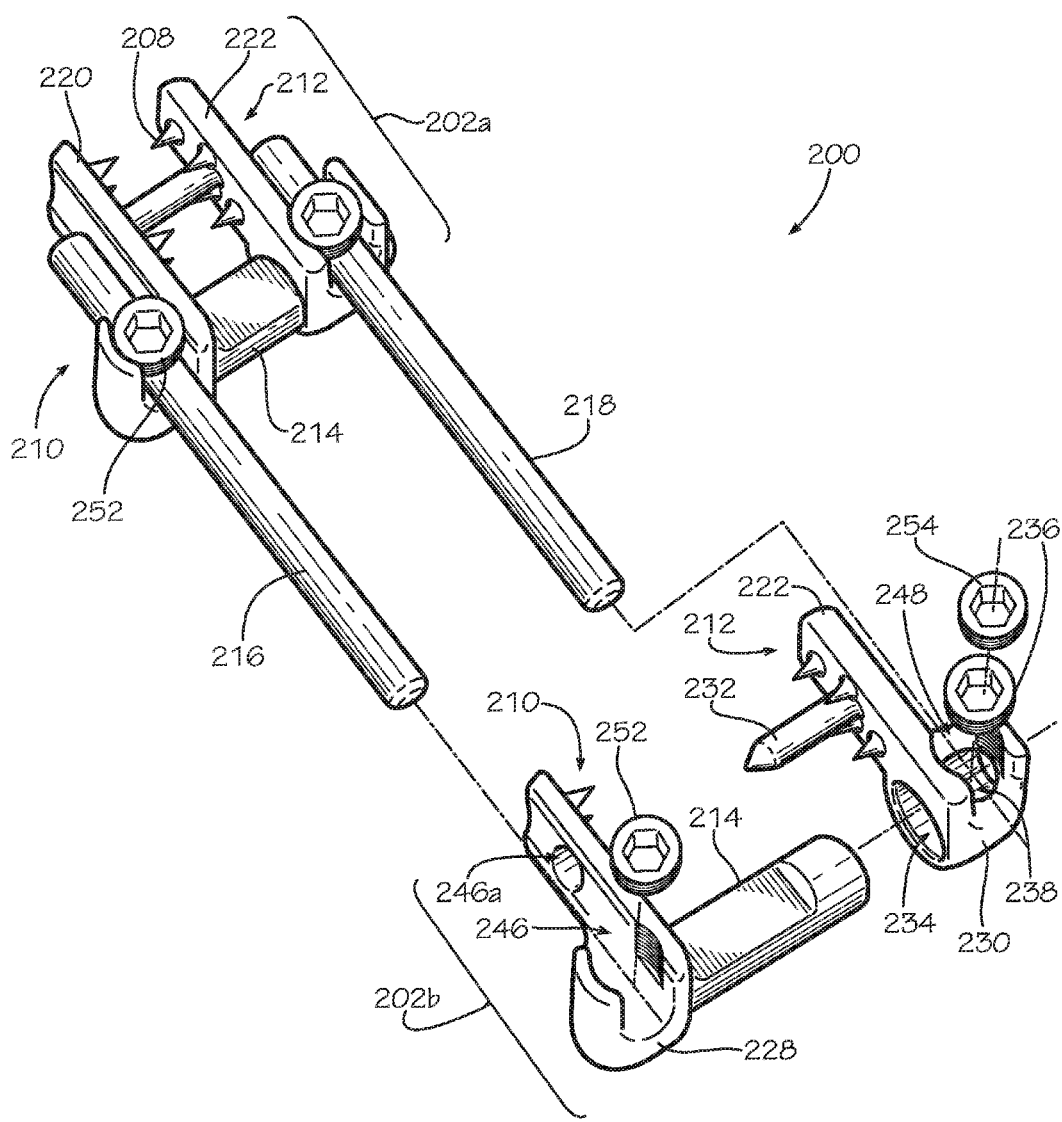
FIG. 9 is a partially exploded perspective view of an alternative embodiment of a spinous process fixation device in accordance with the present invention.

In various other embodiments, a spinous process clamp 202 in accordance with the present invention includes a configuration as seen in FIG. 9 but without a fixation pin 232. In some embodiments, a spinous process fixation device includes first and second rods 216, 218 and first and second spinous process clamps 202a, 202b disposed on first and second rods, wherein one of first and second spinous process clamps 202a, 202b includes a fixation pin 232 and one does not.

Figure 10:
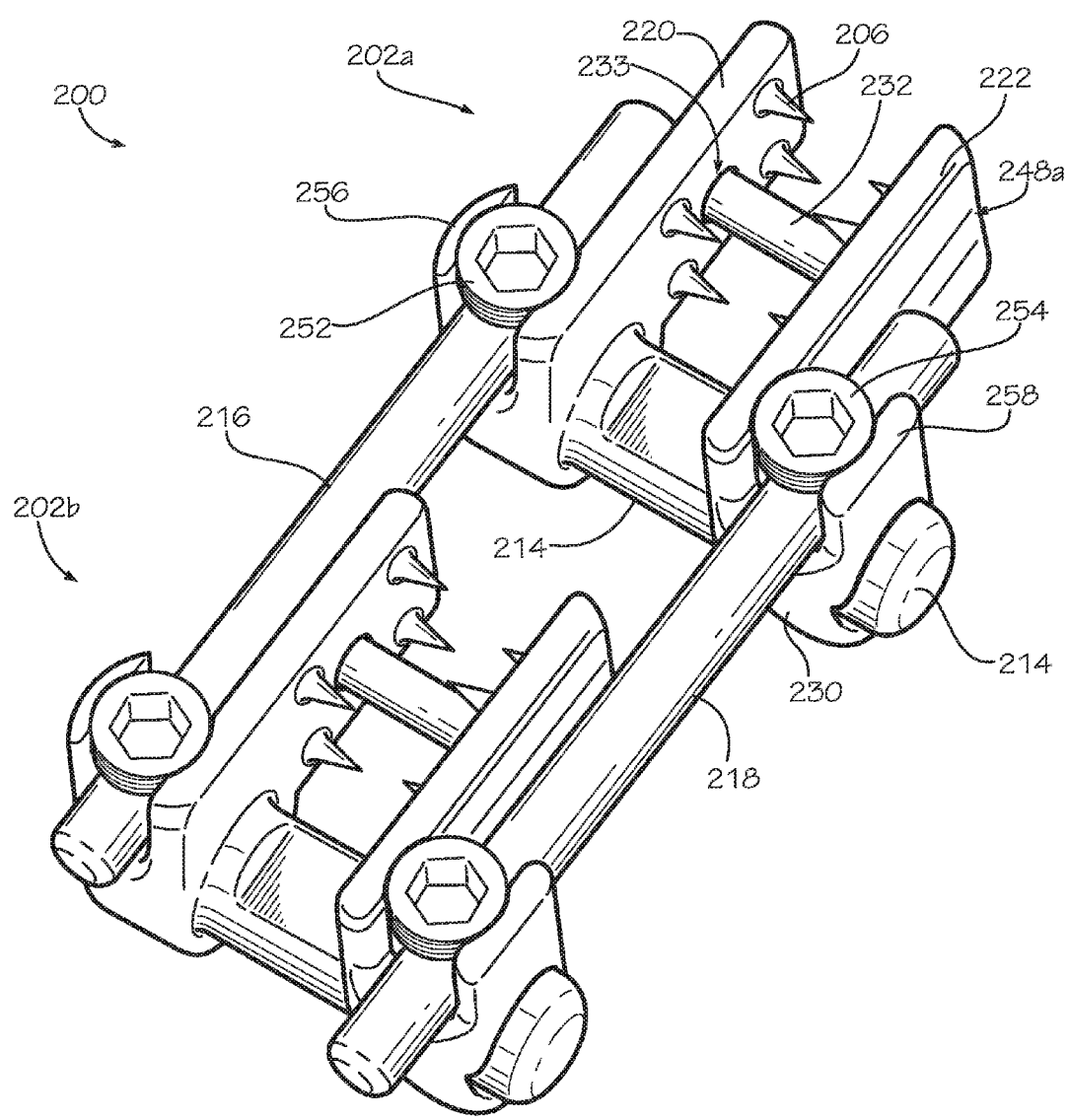
FIG. 10 is a perspective view of the embodiment of a spinous process fixation device of FIG. 9.

Referring further to FIG. 9 and FIG. 10, a primary rod channel 246 is defined through primary block 210. Primary rod channel 246 generally defines a U-shaped opening positioned for partially receiving a portion of a first rod 216. Primary rod channel 246 extends entirely through primary block 210 because it is open at both longitudinal ends, as seen in FIG. 9. A portion of primary rod channel 246a may also be defined in primary clamp plate 220 as a groove or recession on the side of primary clamp plate 220 facing away from secondary block 212 in some embodiments. As such, during use, primary clamp plate 220 is located between first rod 216 and secondary block 212. In this configuration, first rod 216 applies a lateral force against primary clamp plate 220 directed inwardly toward the spinous process member, as seen in FIG. 11.

Similarly, a secondary rod channel 248 is defined through secondary block 212. Secondary rod channel 248 includes a U-shaped opening for partially receiving second rod 218. Secondary rod channel 248 extends entirely through secondary block 212 because secondary rod channel 248 is open at both longitudinal ends, as seen in FIG. 9. A portion of secondary rod channel 248a is defined in secondary block 212 in the surface of secondary clamp plate 222 facing away from primary block 210 as a groove or recess in some embodiments, as seen in FIG. 10. As such, primary clamp plate 222 is located between second rod 218 and primary block 210 during use. In this configuration, second rod 218 applies a lateral force against secondary clamp plate 222 directed inwardly toward a spinous process member.

Referring further to FIG. 9 and FIG. 10, a first rod fastener 252 is disposed on primary block 210 for securing primary block 210 to first rod 216. First rod fastener 252 includes a set screw or any other suitable fastener in some embodiments. In some embodiments, a primary flange 228 extends outwardly from primary clamp plate 222. Primary flange 228 is integrally formed on primary block 210 in some embodiments. A primary tab 256 extends upwardly from primary flange 228 on primary block 210. A space is defined between primary tab 256 and primary clamp plate 220. A threaded primary rod fastener bore is defined between a surface on primary tab 256 and the outer surface on primary clamp plate 220 in some embodiments. The U-shaped primary rod channel 246 extends between primary tab 256 and primary clamp plate 220. Thus, first rod 216 is received between primary tab 256 and primary clamp plate 220, and primary fastener 252 is screwed into the space between primary tab 256 and first clamp plate 220 generally toward first rod 216. As seen in FIG. 9 and FIG. 10, clamp post 214 and primary flange 228 are aligned and extend from opposite sides of primary clamp plate 220 in some embodiments.

Referring further to FIGS. 9-12, in some embodiments, a secondary flange 230 protrudes from secondary clamp plate 222 generally in the direction away from primary block 210. Secondary flange 230 includes clamp post socket 234 defined therethrough in some embodiments. A secondary tab 258 extends upwardly from secondary flange 230 in some embodiments. U-shaped secondary rod channel 248 extends through the space between secondary tab 258 and secondary clamp plate 222 such that second rod 218 may be slidably received between secondary tab 258 and secondary clamp plate 222. During use, clamp post 214 is inserted into clamp post socket 234, and a clamp post fastener 236 is screwed into clamp post fastener bore 238. Clamp post fastener 236 is dimensioned such that it does not extend upwardly into secondary rod channel 248 when tightened against clamp post 214. Second rod 218 may then be installed in secondary rod channel 248, and secondary rod fastener 254 is screwed into the space between secondary tab 258 and secondary clamp plate 222 and is tightened against second rod 218.

In some embodiments, a secondary rod fastener bore is coaxially aligned with clamp post fastener bore 238 such that second rod fastener 254 is positioned directly above, or aligned co-axially with, clamp post fastener 236, as seen in FIG. 9. In other embodiments, these can be slightly offset.

Figure 13:
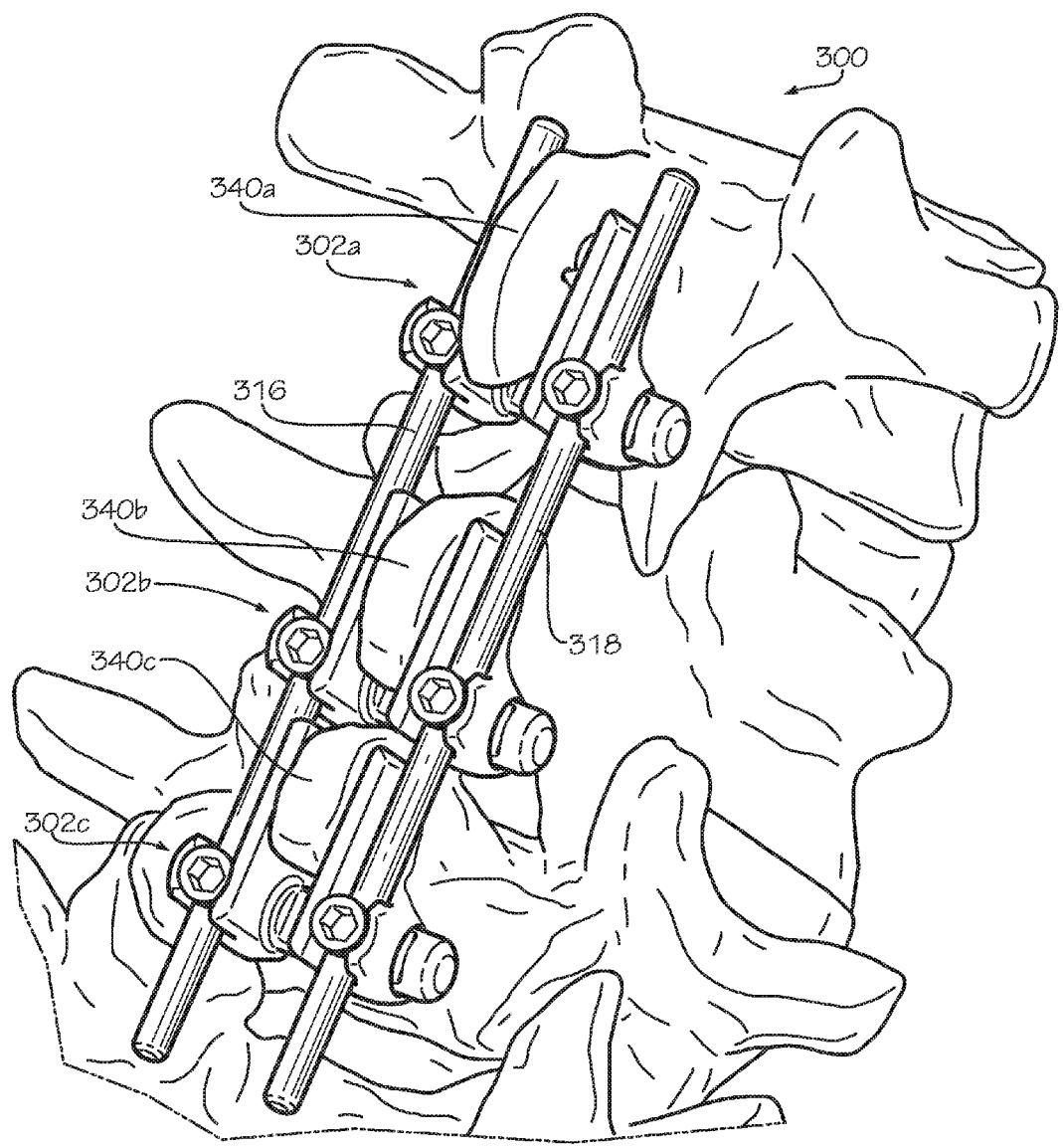
FIG. 13 is a perspective view of an alternative embodiment of a spinous process fixation device including three spinous process clamps.
Figure 14:
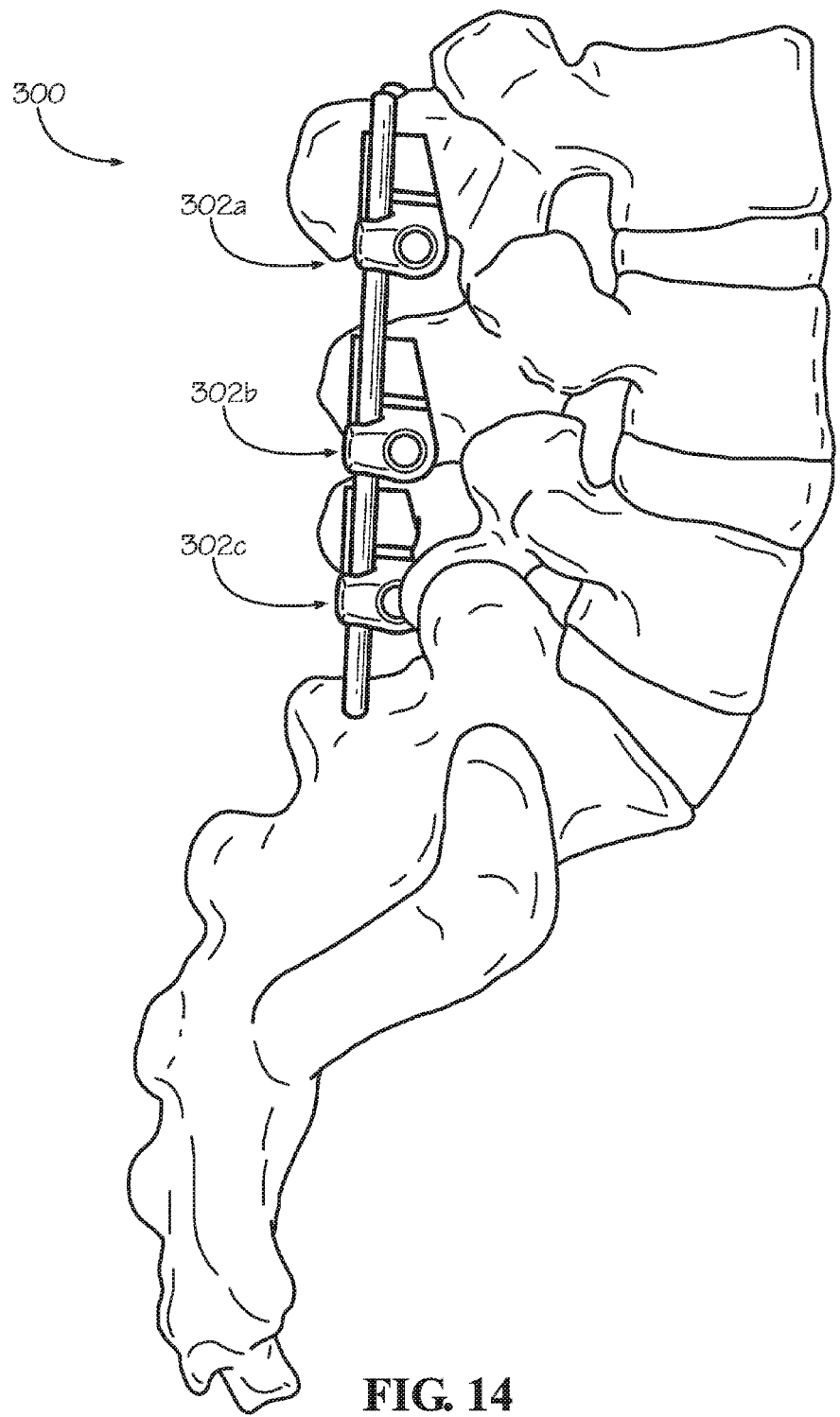
FIG. 14 is a side view of the embodiment of a spinous process fixation device of FIG. 13.

Referring to FIG. 13 and FIG. 14, an additional example of a spinous process fixation assembly 300 includes a pair of opposing longitudinal first and second rods 316, 318 with three or more spinous process clamps 302a, 302b, 302c, etc. mounted thereon. Each spinous process clamp can include any of the various aforementioned clamp embodiments. In some embodiments, not all of the spinous process clamps are the same. For example, in some embodiments, a spinous process fixation device includes a first spinous process clamp 102, seen in FIG. 6 and a second spinous process clamp 202 seen in FIG. 9.

Thus, although there have been described particular embodiments of the present invention of a new and useful Spinous Process Clamp and Fixation Device, it is not intended that such references be construed as limitations upon the scope of this invention except as set forth in the following claims.

What is claimed is:

1. A spinous process clamp apparatus configured for attachment to first and second longitudinal rods positioned on opposite sides of a spinous process member, the apparatus comprising:
    a primary block including a primary clamp plate and a primary rod channel, the primary rod channel shaped for receiving the first longitudinal rod against the primary clamp plate;
    a secondary block opposite the primary block, the secondary block including a secondary clamp plate and a secondary rod channel, the secondary rod channel shaped for receiving the second longitudinal rod against the secondary clamp plate;
    a clamp post protruding from the primary block, the secondary block movable along the clamp post;
    a primary rod fastener disposed on the primary block configured to secure the primary block at a desired location on the first longitudinal rod;
    a secondary rod fastener disposed on the secondary block configured to secure the secondary block at a desired location on the second longitudinal rod;
    a clamp post socket defined on the secondary block, wherein the clamp post extends from the primary block toward the secondary block and is received in the clamp post socket;
    a clamp post fastener disposed on the secondary block, the clamp post fastener configured to secure the secondary block to the clamp post; and
    wherein the primary and secondary clamp plates are configured to apply compressive forces against opposite sides of the spinous process member when the spinous process member is positioned between the primary and secondary clamp plates,
    wherein the primary rod channel is defined in a side of the primary clamp plate facing away from the secondary block, the primary rod channel extending entirely through the primary block along a longitudinal axis of the primary block, and the secondary rod channel is defined in a side of the secondary clamp plate facing away from the primary block, the secondary rod channel extending entirely through the secondary block along a longitudinal axis of the secondary block.

2. The apparatus of claim 1, wherein:
    the primary and secondary rod fasteners are set screws.

3. The apparatus of claim 1, wherein:
    the clamp post is integrally formed on the primary block in a unitary one-piece construction.

4. The apparatus of claim 1, wherein:
    the clamp post fastener is a set screw.

5. The apparatus of claim 1, wherein:
the clamp post fastener and the secondary rod fastener are co-axially aligned.

6. The apparatus of claim 5, further comprising:
a fixation pin extending from the secondary clamp plate toward the primary clamp plate, the fixation pin configured to puncture and extend through the spinous process member when the spinous process member is received between the primary and secondary clamp plates.

7. The apparatus of claim 1, further comprising:
the clamp post extending from the primary block toward the secondary block; and
a fixation pin extending from the secondary clamp plate toward the primary clamp plate, the fixation pin configured to puncture and extend through the spinous process member when the spinous process member is received between the primary and secondary clamp plates.

8. A spinous process fixation device for attachment to at least one spinous process member, the device comprising:
a first longitudinal rod;
a second longitudinal rod oriented substantially parallel to the first longitudinal rod;
a primary block disposed on the first longitudinal rod;
a secondary block disposed on the second longitudinal rod opposite the primary block;
a gap defined between the primary and secondary blocks configured to receive the spinous process member; and
a clamp post located on the primary block, the clamp post spanning the gap between the primary and secondary blocks;
a clamp post socket defined in the secondary block, the clamp post socket configured to slidably receive the clamp post;
a fixation pin integrally formed on the secondary block, the fixation pin spanning the gap between the primary and secondary blocks;
a fixation pin socket defined in the primary block, the fixation pin socket configured to slidably receive the fixation pin;
wherein the primary and secondary blocks are configured to apply compressive forces against opposite sides of the spinous process member, the fixation pin positioned to pierce and extend through the spinous process member as the secondary block is pressed toward the primary block.

9. The apparatus of claim 8, wherein:
the clamp post extend from the primary block toward the secondary block; and
the clamp post socket defined in the secondary block is aligned substantially perpendicular to the second longitudinal rod.

10. The apparatus of claim 8, further comprising:
a clamp post fastener disposed on the secondary block configured to secure the secondary block to the clamp post.

11. The apparatus of claim 10, further comprising:
a secondary rod fastener disposed on the secondary block.

12. The apparatus of claim 11, wherein:
the secondary rod fastener is co-axially aligned with the clamp post fastener.

13. A spinous process fixation device for attachment to a plurality of spinous process members, comprising:
a first longitudinal rod;
a second longitudinal rod oriented substantially parallel to the first longitudinal rod; and
a plurality of spinous process clamps disposed on the first and second longitudinal rods;
wherein each spinous process clamp comprises:
a primary block disposed on the first longitudinal rod;
a secondary block disposed on the second longitudinal rod opposite the primary block;
a plurality of primary spikes located on the primary block and extending toward the secondary block;
a plurality of secondary spikes located on the secondary block and extending toward the primary block;
a clamp post located on the primary block and extending toward the secondary block; and
a fixation pin integrally formed on the secondary block and extending toward the primary block.

14. The device of claim 13, further comprising:
the clamp post extending from the primary block;
a clamp post socket defined in the secondary block, the clamp post received in the clamp post socket; and
a clamp post fastener disposed on the secondary block configured to secure the secondary block to the clamp post.

15. The device of claim 13,
wherein the fixation pin is positioned to pierce and extend through one of the plurality of spinous process members.

\* \* \* \* \*